(12) United States Patent
Zhang et al.

(10) Patent No.: US 11,618,737 B2
(45) Date of Patent: *Apr. 4, 2023

(54) HYDROLYSIS METHOD FOR TERT-BUTYL ESTER IN GADOLINIUM-BASED CONTRAST AGENT

(71) Applicant: HUBEI TIANSHU PHARMACEUTICAL CO., LTD, Hubei (CN)

(72) Inventors: Zhihua Zhang, Hubei (CN); Yunlong Liu, Hubei (CN)

(73) Assignee: HUBEI TIANSHU PHARMACEUTICAL CO., LTD, Yicheng (CN)

( * ) Notice: Subject to any disclaimer, the term of this patent is extended or adjusted under 35 U.S.C. 154(b) by 329 days.

This patent is subject to a terminal disclaimer.

(21) Appl. No.: 16/761,178

(22) PCT Filed: Jan. 29, 2019

(86) PCT No.: PCT/CN2019/073688
§ 371 (c)(1),
(2) Date: May 1, 2020

(87) PCT Pub. No.: WO2020/154891
PCT Pub. Date: Aug. 6, 2020

(65) Prior Publication Data
US 2021/0179568 A1    Jun. 17, 2021

(30) Foreign Application Priority Data

Jan. 28, 2019   (CN) .......................... 201910078756.0

(51) Int. Cl.
*B01J 21/06* (2006.01)
*C07D 257/02* (2006.01)
*B01J 21/08* (2006.01)
*B01J 37/04* (2006.01)
*B01J 37/06* (2006.01)
*B01J 37/08* (2006.01)
*C07C 227/18* (2006.01)

(52) U.S. Cl.
CPC .......... *C07D 257/02* (2013.01); *B01J 21/063* (2013.01); *B01J 21/066* (2013.01); *B01J 21/08* (2013.01); *B01J 37/04* (2013.01); *B01J 37/06* (2013.01); *B01J 37/08* (2013.01); *C07C 227/18* (2013.01)

(58) Field of Classification Search
None
See application file for complete search history.

(56) References Cited

U.S. PATENT DOCUMENTS 4,791,089 A * 12/1988 Dombro ................... B01J 21/08
502/239

FOREIGN PATENT DOCUMENTS

| CN | 103068790 A | 4/2013 |
|---|---|---|
| CN | 109705104 A | 5/2019 |

OTHER PUBLICATIONS

Valencic, M. Tetrahedron Letters, 39, 1995, 1625.*

* cited by examiner

*Primary Examiner* — Clinton A Brooks
(74) *Attorney, Agent, or Firm* — TraskBritt

(57) ABSTRACT

A hydrolysis method for tert-butyl ester in gadolinium-based contrast agent comprises hydrolyzing the tert-butyl ester with a catalyst. The preparation method of the catalyst comprises the following steps: subjecting zirconia and titanium tetrachloride to reaction in the presence of sulfuric acid and water at 60° C. to 90° C. until solids are dissolved, adding silica to perform reaction for 1 to 5 h, filtering to obtain solids, washing and calcining the solids. This hydrolysis method does not introduce other substances that are difficult to remove, such as acids, and provides high hydrolysis efficiency and high purity of the obtained product.

1 Claim, No Drawings

HYDROLYSIS METHOD FOR TERT-BUTYL ESTER IN GADOLINIUM-BASED CONTRAST AGENT

CROSS-REFERENCE TO RELATED APPLICATIONS

This application is a national phase entry under 35 U.S.C. § 371 of International Patent Application PCT/CN2019/073688, filed Jan. 29, 2019, which claims the benefit under Article 8 of the Patent Cooperation Treaty to Chinese Patent Application Serial No. 2019100787560, filed Jan. 28, 2019.

TECHNICAL FIELD

The present disclosure relates to the technical field of contrast agents for diagnostic imaging, and more particularly, to a hydrolysis method for the tert-butyl ester in a gadolinium-based contrast agent.

BACKGROUND

Nuclear Magnetic Resonance Imaging (NMRI), also known as Magnetic Resonance Imaging (MRI), has become a conventional diagnostic technology in clinical medical diagnosis due to its advantages such as non-invasiveness, high-resolution anatomical imaging, and nontoxicity and harmlessness to living organisms. NMRI is based on the relaxation of water protons in the human body from high-energy hydrogen nuclei to low-energy nuclei under an external magnetic field to generate image. The image quality is affected by the density and distribution of water protons in the human body. In many cases, it is difficult to reach a clear Mill anatomy map, so it is difficult to accurately judge the disease and injury. The contrast agent can change the relaxation time of the surrounding water protons, increase the magnetic resonance contrast between the detection target site and the surrounding background tissue, and improve the sensitivity and accuracy of NMRI.

So far, gadolinium-centered-complex-based targeting magnetic resonance technology has been most widely used in clinic. The outer layer of gadolinium (Gd) has 7 unpaired electrons, so it is a powerful paramagnetic ion. Non-complexed gadolinium ions are toxic, but the toxic effect of gadolinium can be almost completely eliminated without significantly affecting its paramagnetic effect after the gadolinium forms a complex with a non-toxic organic chelating agent. Various chelating agents of gadolinium that can be injected intravenously have become an integral part of magnetic resonance imaging (MRI) technology, such as gadobutrol or gadoteridol.

A variety of preparation methods of gadolinium chelating agents have been described in the prior art. These preparation methods relate to a step of converting an ester containing a nitrogen atom into an acid. In this step, an acid is usually used to convert the ester into an acid. At the same time, a resin is used to separate the target product from impurities. This step makes the entire production process high in cost, low in yield, and low in purity of the target product in large-scale production.

BRIEF SUMMARY

A first purpose of the present disclosure is to provide a hydrolysis method for tert-butyl ester in gadolinium-based contrast agent, comprising the step of hydrolyzing the tert-butyl ester with a catalyst, wherein the catalyst is prepared by a method comprising the following steps: subjecting zirconia and titanium tetrachloride to reaction in the presence of sulfuric acid and water at 60° C. to 90° C. until solids are dissolved, adding silica to perform reaction for 1 to 5 h, filtering to obtain the solid, and washing and calcining the solid.

In a preferred embodiment of the present disclosure, the molar ratio of the zirconia to titanium tetrachloride is 1:(0.1-1), preferably 1:(0.4-0.5).

In a preferred embodiment of the present disclosure, the volume ratio of the sulfuric acid to water is (0.5-3):10, preferably (1-1.5):10.

In a preferred embodiment of the present disclosure, the mass to volume ratio of the zirconia to silica is 1:(10-20), preferably 1:(12-15).

In a preferred embodiment of the present disclosure, the calcination temperature is 500° C. to 700° C., preferably 550° C. to 600° C.

In a preferred embodiment of the present disclosure, the tert-butyl ester is (s)-di-tert-butyl-2,2'-((2-((2-bis(2-(tert-butoxy)-2-oxoethyl)amino)-3-(4-ethoxyphenyl)propyl)(2-(tert-butoxy)-2-oxoethyl)amino)ethyl)aza)diacetate, or a compound having the structure shown in any one of the general formulae (I) to (III):

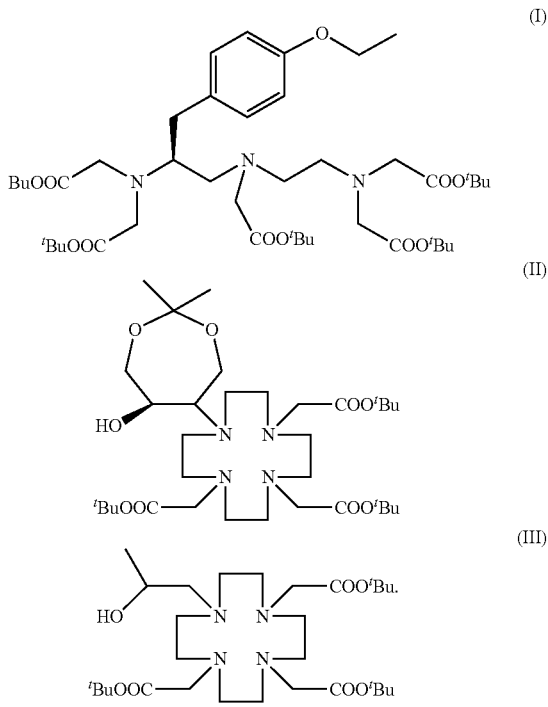

In a preferred embodiment of the present disclosure, the mass ratio of the tert-butyl ester to the catalyst is 1:(1-1000), preferably 1:(50-100), and more preferably 1:100.

In a preferred embodiment of the present disclosure, the hydrolysis temperature is 70° C. to 90° C., and the hydrolysis time is 8 to 24 h. More preferably, the hydrolysis temperature is 85° C. to 90° C., and the hydrolysis time is 12 to 15 h.

In the above hydrolysis reaction, the weight ratio of the added water to the tert-butyl ester is 20:1 to 20:5.

In a preferred embodiment of the present disclosure, the hydrolysis may specifically comprise: mixing the abovementioned tert-butyl ester with water, adding the above catalyst to react at 70° C. to 90° C. for 8 to 24 h.

After the end of the hydrolysis reaction, the reaction solution may be filtered, washed with water, concentrated and then recrystallized using ethanol and/or acetone.

Another purpose of the present disclosure is to provide a catalyst for hydrolyzing tert-butyl ester in gadolinium-based contrast agent. The preparation method of the catalyst comprises the following steps: subjecting zirconia and titanium tetrachloride to reaction in the presence of sulfuric acid and water at 60° C. to 90° C. until solids are dissolved, adding silica to perform reaction for 1 to 5 h, filtering to obtain the solid, washing and calcining the solid. The optimization of other conditions is as described in the related contents above, and is not repeated herein.

The hydrolysis method of the present disclosure does not introduce other substances that are difficult to remove, such as acids, and provides high hydrolysis efficiency and high purity of the obtained product (the purity is greater than 98%, and the yield is greater than 88%, more preferably, the purity is greater than 99%, and the yield is greater than 90%). The production cost in the preparation process of the gadolinium-based contrast agent is greatly reduced, and the waste gas, waste water and waste residues produced in the preparation process are effectively reduced.

DETAILED DESCRIPTION

The specific embodiments of the present disclosure will be described in further detail in combination with the Examples below. The following Examples are used to illustrate the present disclosure, but not to limit the scope of the present disclosure.

Unless otherwise specified, the technical means used in the Examples are conventional means well known to a person skilled in the art, and the raw materials used are all commercially available products.

Example 1

The present Example provides a hydrolysis method for tert-butyl ester in gadolinium-based contrast agent. The reaction equation is as follows:

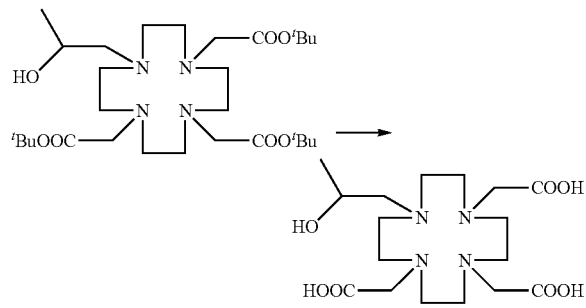

The hydrolysis method provided in the present Example comprises the following steps:

The compound represented by formula (III) was added into a 500 mL reaction flask containing 200 mL distilled water, and a catalyst was added under stirring (the mass ratio of the compound represented by formula (III) to the catalyst was 1:100) to perform reaction at 90° C. for 12 h, and then the resultant was filtered, washed with a small amount of water, concentrated to dry under reduced pressure, and recrystallized with 95% ethanol to obtain 17 g white solid of teridol.

Wherein, the catalyst was prepared by the following method: 5 g $ZrO_2$ and 3 g $TiCl_4$ were added to 100 mL distilled water, and 10 mL sulfuric acid was added; the mixture was heated at about 80° C. until the solid were completely dissolved, and then 60 ml $SiO_2$ was added to perform adsorption for 2 h; and the resultant was filtered, washed twice with water, washed twice with 50 mL of 10% NaOH, and washed with distilled water to neutrality, and then calcined at 550° C. to obtain the catalyst.

The purity of the teridol obtained in the present Example is 99.8%, and the yield is 96%. The elemental analysis results of the product obtained in the present Example are as follows: C: 50.37%, N: 13.80%, and H: 8.09%, $C_{17}H_{32}N_4O_7$ theoretical values: C: 50.44%, N: 13.85%, and H: 8.01%; wherein, both the infrared spectrum and the nuclear magnetic resonance hydrogen spectrum of the product obtained in the present Example indicate that the obtained substance is teridol.

Example 2

The present Example provides a hydrolysis method for tert-butyl ester in gadolinium-based contrast agent. The reaction equation is as follows:

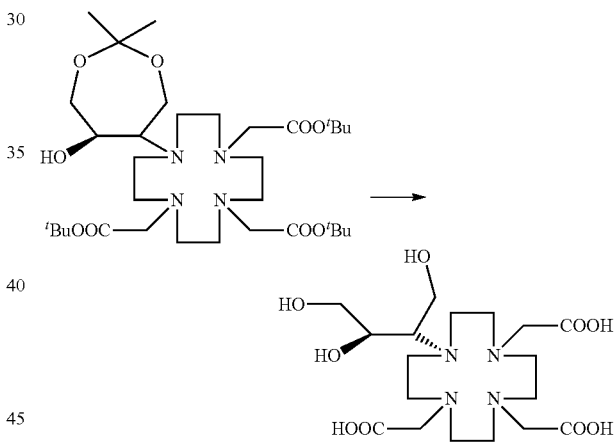

The steps were the same as those in Example 1, except that the tert-butyl ester was a compound represented by formula (II); and the solvent for recrystallization was ethanol/acetone (6:4). 21 g butrol was obtained in the present Example.

The purity of the butrol obtained in the present Example is 99.7%, and the yield is 95%. The elemental analysis results of the product obtained in the present Example are as follows: C: 47.82%, N: 12.32%, and H: 7.64%, $C_{18}H_{34}N_4O_9$ theoretical values: C: 47.97%, N: 12.43%, and H: 7.62%; wherein, both the infrared spectrum and the nuclear magnetic resonance hydrogen spectrum of the product obtained in the present Example indicate that the obtained substance is butrol.

Example 3

The present Example provides a hydrolysis method for tert-butyl ester in gadolinium-based contrast agent. The reaction equation is as follows:

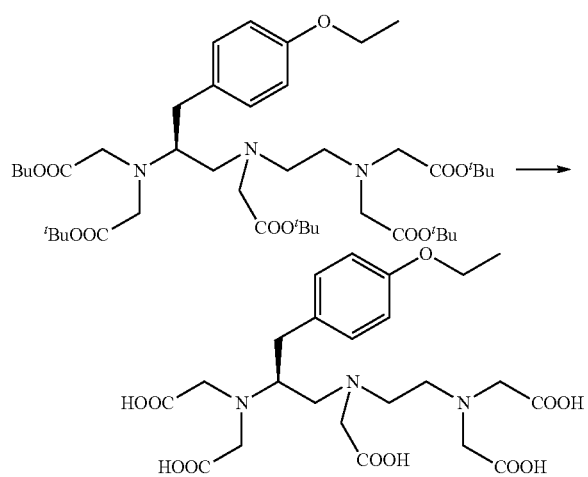

The steps were the same as those in Example 1, except that the tert-butyl ester was a compound represented by formula (I).

The purity of the product obtained in the present Example is 99%, and the yield is 96%. 1H-NMR (400 MHZ) (DMSO-d6) δ: 1.31 (t (7 Hz), 2.47 (dd (14.7 Hz), 1H), 2.78-2.90 (m, 4H), 2.90-3.10 (m, 3H), 3.20-3.50 (m, 9H), 3.60-3.75 (m, 2H), 3.99 (q (7 Hz), 2H), 6.80-6.85 (m, 2H), 7.10-7.15 (m, 2H), 8-12 (m, 5H).

Example 4

The present Example provides a hydrolysis method for tert-butyl ester in gadolinium-based contrast agent. The reaction equation is as follows:

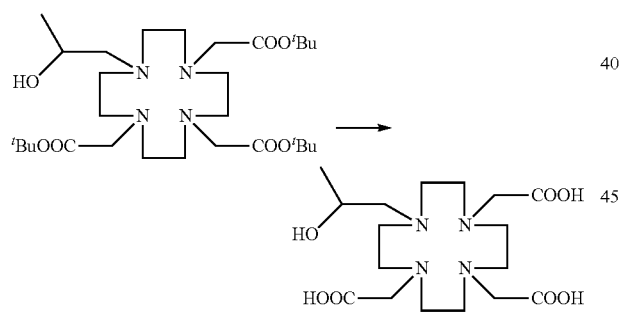

The hydrolysis method provided in the present Example comprises the following steps:

The compound represented by formula (III) was added into a 500 mL reaction flask containing 200 mL distilled water, and a catalyst was added under stirring (the mass ratio of the compound represented by formula (III) to the catalyst was 1:1) to perform reaction at 70° C. for 24 h, and then the resultant was filtered, washed with a small amount of water, concentrated to dry under reduced pressure, and recrystallized with 95% ethanol to obtain a white solid, wherein the catalyst used was the same as that used in Example 1. The elemental analysis results, the infrared spectrum, and the nuclear magnetic resonance hydrogen spectrum of the teridol obtained in the present Example are the same as those in Example 1. The purity of the teridol obtained in the present Example is 99%, and the yield is 90%.

Example 5

The present Example provides a hydrolysis method for tert-butyl ester in gadolinium-based contrast agent. The reaction equation is as follows:

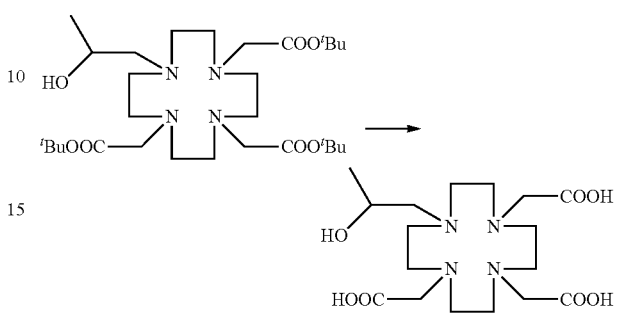

The hydrolysis method provided in the present Example comprises the following steps:

The compound represented by formula (III) was added into a 500 mL reaction flask containing 200 mL distilled water, and a catalyst was added under stirring (the mass ratio of the compound represented by formula (III) to the catalyst is 1:50) to perform reaction at 90° C. for 15 h, and then the resultant was filtered, washed with a small amount of water, concentrated to dry under reduced pressure, and recrystallized with 95% ethanol to obtain a white solid, wherein the catalyst used was the same as that used in Example 1. The elemental analysis results, the infrared spectrum, and the nuclear magnetic resonance hydrogen spectrum of the teridol obtained in the present Example are the same as those in Example 1. The purity of the teridol obtained in the present Example is 99.5%, and the yield is 92%.

Example 6

The present Example provides a hydrolysis method for tert-butyl ester in gadolinium-based contrast agent. The reaction equation is as follows:

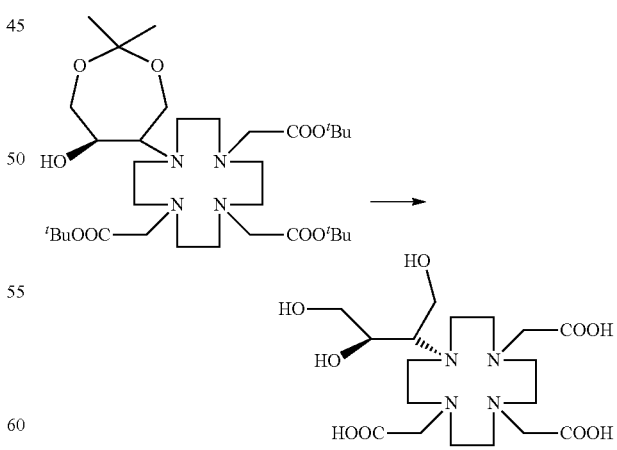

The steps were the same as those in Example 5, except that the tert-butyl ester was a compound represented by formula (II); and the solvent for recrystallization was ethanol/acetone (6:4). The purity of the butrol obtained in the present Example is 99.5%, and the yield is 93%. The elemental analysis results, the infrared spectrum, and the nuclear magnetic resonance hydrogen spectrum of the product obtained in the present Example are the same as those in Example 2.

Example 7

The present Example provides a hydrolysis method for tert-butyl ester in gadolinium-based contrast agent. The reaction equation is as follows:

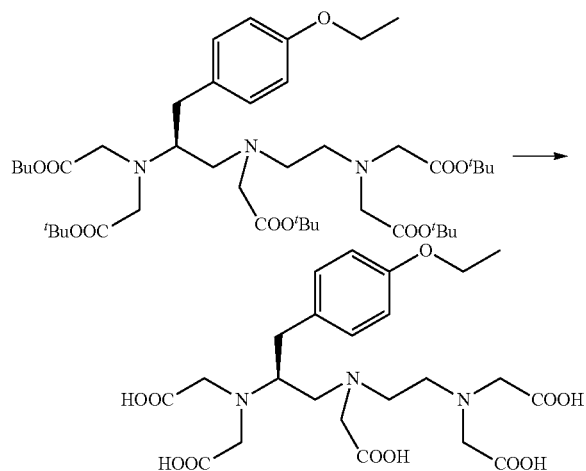

The steps were the same as those in Example 5, except that the tert-butyl ester was a compound represented by formula (I). The purity of the product obtained in the present Example is 99%, and the yield is 90%. The elemental analysis results, the infrared spectrum, and the nuclear magnetic resonance hydrogen spectrum of the product obtained in the present Example are the same as those in Example 3.

Example 8

The present Example provides a hydrolysis method for tert-butyl ester in gadolinium-based contrast agent. The steps are the same as those in Example 1, except that the catalyst used in the present Example was prepared by the following method: 5 g $ZrO_2$ and 0.76 g $TiCl_4$ were added to 100 mL distilled water, and 5 mL sulfuric acid was added; the mixture was heated at about 80° C. until the solid was completely dissolved, 50 ml $SiO_2$ was added to perform adsorption for 2 h; and the resultant was filtered, washed twice with water, washed twice with 50 mL of 10% NaOH, and washed with distilled water to neutrality, and then calcined at 500° C. to obtain the catalyst.

The elemental analysis results, the infrared spectrum, and the nuclear magnetic resonance hydrogen spectrum of the teridol obtained in the present Example are the same as those in Example 1. The purity of the teridol obtained in the present Example is 99%, and the yield is 88%.

Example 9

The present Example provides a hydrolysis method for tert-butyl ester in gadolinium-based contrast agent. The steps were the same as those in Example 1, except that the catalyst used in the present Example was prepared by the following method: 5 g $ZrO_2$ and 7.59 g $TiCl_4$ was added to 100 mL distilled water, and 30 mL sulfuric acid was added; the mixture was heated at about 80° C. until the solid was completely dissolved, 100 ml $SiO_2$ was added to perform adsorption for 2 h; and the resultant was filtered, washed twice with water, washed twice with 50 mL of 10% NaOH, and washed with distilled water to neutrality, and then calcined at 700° C. to obtain the catalyst.

The elemental analysis results, the infrared spectrum, and the nuclear magnetic resonance hydrogen spectrum of the teridol obtained in the present Example are the same as those in Example 1. The purity of the teridol obtained in the present Example is 98.5%, and the yield is 90%.

Finally, the methods described in the embodiments are only preferred embodiments, and are not intended to limit the protection scope of the present disclosure. Any modification, equivalent replacement, or improvement made within the spirit and principle of the present disclosure shall be included in the protection scope of the present disclosure.

INDUSTRIAL APPLICABILITY

The present disclosure provides a hydrolysis method for tert-butyl ester in gadolinium-based contrast agent. The hydrolysis method includes the step of hydrolyzing the tert-butyl ester with a catalyst, wherein the the catalyst is prepared by a method including the following steps: subjecting zirconia and titanium tetrachloride to reaction in the presence of sulfuric acid and water at 60° C. to 90° C. until the solids is dissolved, adding silica to perform reaction for 1 to 5 h, filtering to obtain the solid, washing and calcining the solid. The hydrolysis method provided by the present disclosure can be used for industrial large-scale production, and makes up for the shortcomings of the existing method such as suitability for small-scale production only, insufficient purity, and low hydrolysis efficiency.

What is claimed is:

1. A method for preparing a catalyst for hydrolyzing tert-butyl ester in gadolinium-based contrast agent, the method comprising the following steps: subjecting zirconia and titanium tetrachloride to reaction in the presence of sulfuric acid and water at 60° C. to 90° C. until solids are dissolved, adding silica, performing a reaction for 1 to 5 h, filtering to obtain solids, washing and calcining the solids.

* * * * *